(12) United States Patent
Broz

(10) Patent No.: US 7,971,470 B2
(45) Date of Patent: Jul. 5, 2011

(54) METHOD FOR DETECTING CHEMICAL SUBSTANCES IN WHOLE, CLOSED AND/OR SEALED CONTAINERS

(75) Inventor: Joseph S. Broz, Denver, CO (US)

(73) Assignee: Madison Avenue Management Company, Inc., Morristown, NJ (US)

( * ) Notice: Subject to any disclaimer, the term of this patent is extended or adjusted under 35 U.S.C. 154(b) by 469 days.

(21) Appl. No.: 12/101,797

(22) Filed: Apr. 11, 2008

(65) Prior Publication Data

US 2009/0038374 A1  Feb. 12, 2009

Related U.S. Application Data

(60) Provisional application No. 60/911,724, filed on Apr. 13, 2007.

(51) Int. Cl.
*G01N 1/24* (2006.01)
*G01N 1/40* (2006.01)
*G01N 33/02* (2006.01)

(52) U.S. Cl. ............... 73/31.03; 73/23.22; 73/23.34; 73/864.71; 73/864.81

(58) Field of Classification Search ............... 73/23.22, 73/23.34–23.37, 23.41, 31.03, 31.07, 863, 73/864, 864.71, 864.81–864.87
See application file for complete search history.

(56) References Cited

U.S. PATENT DOCUMENTS

| | | | | |
|---|---|---|---|---|
| 1,539,937 | A * | 6/1925 | Cochrane | 73/52 |
| 4,292,839 | A * | 10/1981 | Hartness | 73/49.2 |
| 5,496,741 | A * | 3/1996 | Pawliszyn | 436/163 |
| 5,691,206 | A * | 11/1997 | Pawliszyn | 436/178 |
| 6,042,787 | A * | 3/2000 | Pawliszyn | 422/69 |
| 6,164,144 | A * | 12/2000 | Berg | 73/863.21 |
| 6,405,608 | B1 | 6/2002 | Lindgren et al. | |
| 6,481,301 | B2 * | 11/2002 | Pawliszyn | 73/864.71 |
| 6,911,822 | B2 | 6/2005 | Augustine | |
| 6,941,825 | B2 * | 9/2005 | Pawliszyn | 73/864.87 |
| 6,964,197 | B2 * | 11/2005 | Davis et al. | 73/700 |
| 7,012,427 | B2 | 3/2006 | Augustine | |
| 7,131,341 | B2 * | 11/2006 | Wareham et al. | 73/864.71 |
| 7,231,806 | B2 * | 6/2007 | Jen | 73/23.2 |
| 7,290,438 | B2 | 11/2007 | Head et al. | |
| 7,339,377 | B2 | 3/2008 | Augustine | |
| 7,464,614 | B2 * | 12/2008 | Harvey | 73/863.84 |

(Continued)

OTHER PUBLICATIONS

Gomez-Ariza, J.L. et al.,"Optimization of a two-dimensional on-line coupling for the determination of anisoles in wine using ECD and ICP-MS after SPME-GC separation", Journal of Analytical Atomic Spectrometry, 20, 2005, 883-888. Howland, P.R. et al., "The location of 2,4,6-trichloroanisole in a batch of contaminated wine corks", Australian Journal of Grape and Wine Research, 3, 1997, 141-145.

(Continued)

*Primary Examiner* — David A. Rogers
(74) *Attorney, Agent, or Firm* — e winner & associates, pllc; Ellen P. Winner

(57) ABSTRACT

A non-invasive and non-destructive apparatus and testing method for analytes in sealed containers are provided, which are especially useful for identifying bottles of wine that are contaminated with 2,4,6-trichloroanisole (TCA) without destroying the value of uncontaminated wine by opening the bottles or marring the containers or labeling. The apparatus and method are applicable to non-destructively testing any "stream-of-commerce" containers such as shampoo bottles, aerosol containers, toothpaste tubes, and soft drink cans, and other such containers for the presence of contaminants, explosives, poisons, drugs, and other dangerous or illegal materials. The method provided is orders of magnitude more sensitive than other methods, and can detect the presence of diffused substances at the nanogram per liter (parts-per-billion) level.

19 Claims, 4 Drawing Sheets

U.S. PATENT DOCUMENTS

2002/0182746 A1* 12/2002 Mester et al. ............ 436/178
2006/0019017 A1* 1/2006 Singh et al. ............... 426/574
2007/0209453 A1* 9/2007 Akinbo et al. ........... 73/864.71
2007/0266771 A1* 11/2007 Goldson et al. ............ 73/31.07
2009/0199621 A1* 8/2009 Land, III .................. 73/23.41

OTHER PUBLICATIONS

Martinez-Urunuela, A. et al., "Multiple solid-phase microextraction in a non-equilibrium situation: Application in quantitative analysis of chlorophenols and chloroanisoles related to cork taint in wine", Journal of Chromatography A, 1089, 2005, 31-38.

\* cited by examiner

METHOD FOR DETECTING CHEMICAL SUBSTANCES IN WHOLE, CLOSED AND/OR SEALED CONTAINERS

CROSS-REFERENCE TO RELATED APPLICATIONS

This application claims priority to U.S. provisional patent application Ser. No. 60/911,724, which is incorporated herein to the extent not inconsistent herewith.

BACKGROUND

Methods for testing cork wine bottle stoppers for the presence of 2,4,6-trichloroanisole in a plurality of wine bottles are disclosed in U.S. Pat. No. 7,290,438 for "Automated Apparatus and Method for Testing Cork Wine Bottle Stoppers for the Presence of an Analyte that causes Cork Taint in Bottled Wine," issued to Head et al. on Nov. 6, 2007. These methods utilize electronic "noses" and test only wine corks or stoppers.

Other methods for analyzing volatizable substances are disclosed in U.S. Pat. No. 6,405,608 for "Method and Apparatus for Optimized Sampling of Volatizable Target Substances," issued to Lindgren et al. on Jun. 18, 2002.

The foregoing examples of the related art and limitations related thereto are intended to be illustrative and not exclusive. Other limitations of the related art will become apparent to those of skill in the art upon a reading of the specification and a study of the drawings.

All publications referred to herein are incorporated herein by reference to the extent not inconsistent with the disclosure hereof.

SUMMARY

It would be desirable to be able to test the contents of sealed containers for analytes such as contaminants or dangerous or contraband substances without opening the containers.

For example, sealed bottles of wine may be tainted with human-perceptible amounts (about 10 ng/L$^1$) of 2,4,6-trichloroanisole (hereinafter "TCA"), and other chemicals produced by a mold-mediated chemical reaction of cork bleach or pentachlorophenol to 2,4,6-trichlorophenol and ultimately to TCA.$^2$. It is estimated by various references that 5%-7% of all wines are spoiled by TCA contamination in the wine and/or in the cork, and this applies especially to collected or cellared wines which may exhibit higher percentages of spoilage. It would be advantageous for wine distributors, and re-sellers of wine such as restaurants, to be able to test unopened, corked, wine bottles for TCA contamination before resale. Thus, in an embodiment hereof, a simple apparatus and process for testing single unopened bottles of wine is provided. It would also be advantageous for wine bottlers to be able to test multiple bottles of wine at the same time to determine whether TCA contamination has occurred. Thus, in an embodiment hereof, a modified apparatus and process for testing multiple unopened bottles of wine is also provided.

In broader application, provided herein is a non-invasive and non-destructive apparatus and testing method for analytes in sealed containers. While this test is especially useful for identifying bottles of wine that are contaminated without destroying the value of uncontaminated wine by opening the bottles or marring the container or labeling, there are many other uses for the apparatus and method For example, "stream-of-commerce" containers such as shampoo bottles, aerosol containers, toothpaste tubes, soft drink cans, and other such containers can be non-destructively tested using the apparatus and methods disclosed herein for the presence of explosives, poisons, drugs, hormones, and other dangerous or illegal materials. Other uses for this test include testing of food and drink containers for contamination, such as testing packages of cheese for contaminates such as methane or testing other foods and drinks for spoilage or contamination.

In embodiments, the closed container is a container large enough to hold multiple smaller containers, for example a box containing multiple bottles of wine as shown in FIG. 4 hereof comprising a suction conduit. In that case, the portion of the sealed container that is accommodated within the hollow chamber of the wand is the suction conduit, e.g., element 42 of FIG. 4.

The method provided herein is orders of magnitude more sensitive than other methods, such as nuclear magnetic resonance (NMR) testing methods, and can detect the presence of diffused substances at the nanogram level, achieving a sensitivity that is almost as good as the human nose, which can detect odors at the parts per billion level.

Other uses for the apparatuses and methods disclosed herein include: assuring the quality and safety of foodstuffs in their point-of-sale, stream-of commerce containers. The apparatus and method can also be used by security personnel at airports, train stations, stadium entrances and other checkpoints to check and screen for harmful substances, such as explosives or explosive precursor materials, acids, or flammable materials disguised in normal beverage containers or hidden and contained in other types of typical consumer containers.

In addition to the exemplary aspects and embodiments described above, further aspects and embodiments will become apparent by reference to the drawings and by study of the following descriptions.

BRIEF DESCRIPTION OF THE DETAILED DRAWINGS

Figure 1:
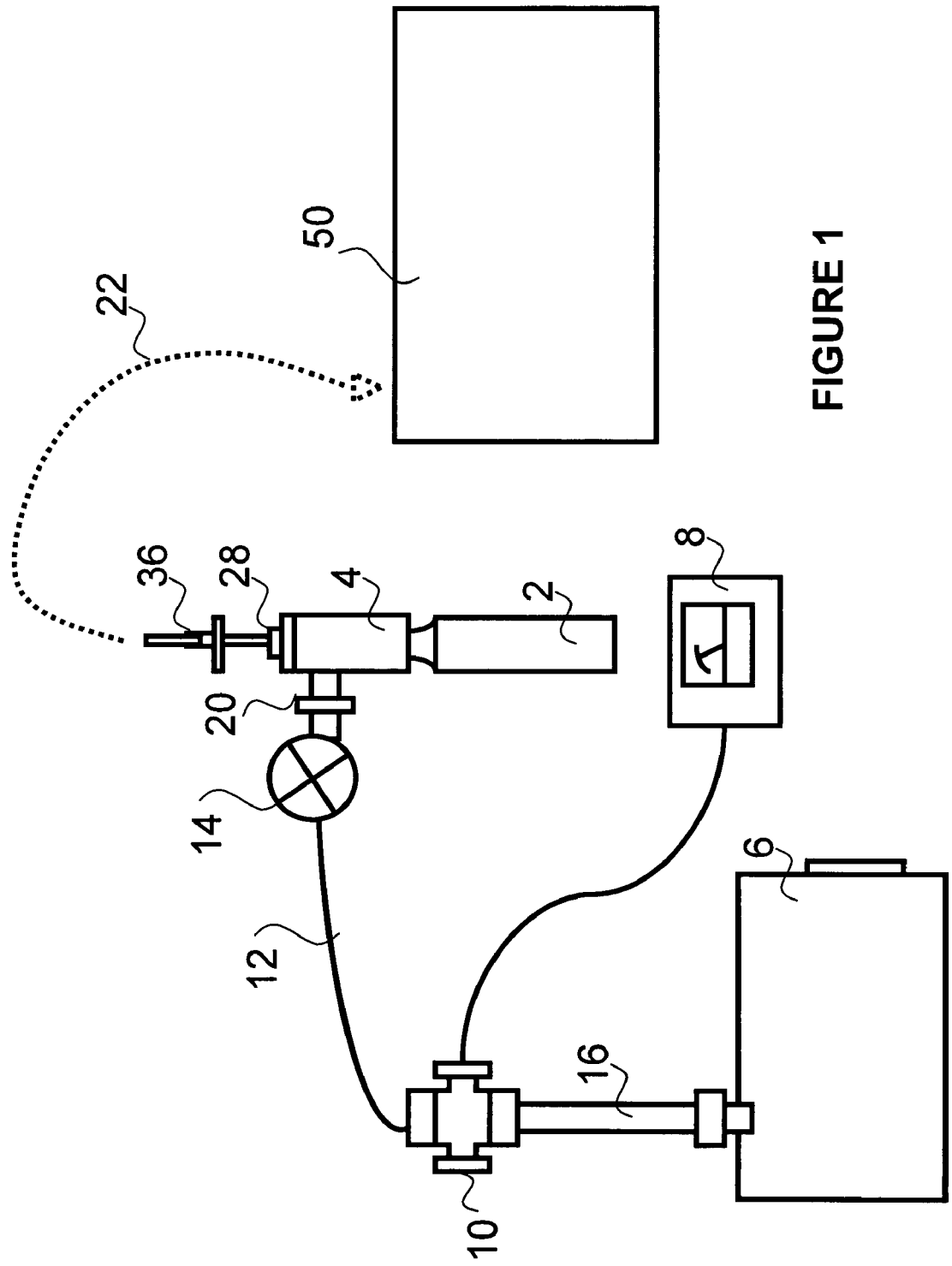
FIG. 1 is a schematic representation of an embodiment of the chemical detection system and process described herein for testing unopened bottles of wine for contamination with 2,4,6-trichloroanisole (TCA).

Exemplary embodiments are illustrated in referenced figures of the drawings. It is intended that the embodiments and figures disclosed herein are to be considered illustrative rather than limiting.

DESCRIPTION

A wand for detecting the presence of an analyte in a closed container without opening the container is provided. The wand comprises: a wall defining a hollow chamber within said wand, wherein said chamber is large enough to accommodate at least a portion of said closed container, leaving a test space within said chamber; a first opening in said wall for receiving at least a portion of said closed container within said chamber; first sealing means operably positioned with respect to said first opening for sealing said first opening so as to prevent air flow in and out of said chamber through said first opening; a second opening in said wall for receiving within said test space at least a portion of an analyte collection material capable of adsorbing or absorbing said analyte within said test space; second sealing means operably positioned with respect to said second opening for sealing said second opening so as to prevent air flow in and out of said chamber through said second opening; a third opening in said wall for receiving a conduit for creating at least a partial vacuum in said test space; third sealing means operably positioned with respect to said third opening for sealing said third opening so as to prevent air flow other than through said conduit in and out of said third opening.

The term "wand" as used herein refers to a component that encloses a hollow space and has the three sealable openings described above. It is hollow and defines a space large enough to receive at least a portion of a closed container to be tested, leaving enough vacant "test space" to accommodate an analyte collection material and a sufficient amount of diffused analyte to be sorbed in measurable amounts on the analyte collection material. In some embodiments it has a length greater than its width, but it can be any size and shape required to receive a specific desired container or portion thereof and the specific analyte collection material utilized. For example very small containers, such as perfume bottles or travel-sized "stream-of-commerce" containers may fit entirely within the wand, while only a portion of larger containers such as wine or detergent bottles may fit inside the wand. The term "stream-of-commerce containers" is known to the art and refers to containers for ordinary consumables such as foods, drinks, toiletries, household chemicals, and the like. As examples of foods and drinks, containers of wines, beers, oils, cheeses and other dairy products, as well as containers of solids, such as nuts, containing volatile or aromatic chemicals (possibly allergenic substances) can be tested for known contaminants.

The analyte to be detected can be a contaminant or a detectable marker of contamination, such as a gas produced by a microorganism, of a substance, such as TCA, a contaminant of wine; methane (or other gases), a marker of cheese contamination; proteins and other volatiles, markers for the allergens contained in peanuts; sulfur compounds and/or sulfuric acid, or a contaminant sometimes found in natural gas pipelines generated by certain methane-consuming bacteria that etches the metal and destroys the physical integrity of the pipeline. The analyte may also be a dangerous or illegal substance such as a component or marker of the presence of a compound such as ricin, or drug or drug precursor component used in the manufacture of methamphetamines, or an explosive or marker of the presence of an explosive such as acetone used in the production of tri-acetone tri-peroxide (TATP); methylethylketone used in the production of the explosive MEKAP, as specific examples.

A closed container can be any container that is closed, meaning that the contents of the container cannot be removed without opening the container. The "contents" of the container in this context do not include the small amount of air or gas, or diffused molecules of analyte material, that can escape from the closed container during the test procedure. Closed containers can include "stream of commerce" containers. The analyte may be inside the container, or may be present on the outside of the container, or in or on the lid or in the case of wine or other materials sealed with corks or other stopper-type materials, in the stopper, or the analyte may be in multiple places in or on the closed container. In the case of containers comprising many substances, such as explosives or other contraband materials, the materials are typically present in small but detectable amounts on the outside of the container due to handling by the persons who placed the contraband materials in the container.

The reference to testing for an analyte "without opening the container" means that the container is not breached in such a way as to allow commercially significant loss of its contents or to introduce contamination into the container. The act of producing a vacuum in the test space of a wand as described herein, such that material inside the container can diffuse out through tiny openings in the container is not considered herein to be "opening the container."

The wall of the wand must be thick enough and made of a strong enough material that it is not broken or significantly deformed by the vacuum produced inside the wand. In the case of a wand used for testing single wine bottles, the wall should be at least about 0.5 mm to 5 mm thick. The wall should also be made of a material that does not significantly adsorb or absorb the analyte to be tested, as this can cause inaccurate measurements. The material of the wand wall should also not evolve chemicals that interfere with measurements. Some suitable materials for the wand walls are stainless steel, titanium, highly polished gold- or platinum-plated metals, Teflon-coated materials, and plastics such as polyethylene, polyester, polyvinyl chloride, cellulose, nylon, Tyvek™, poly-coated material stocks, Kimdura™ and Teslin™, and crystalline plastics such as PPS (polyphenylsulfide) and others that do not significantly adsorb or absorb the analyte to be tested, to mention a few. Other suitable materials can be readily determined by one skilled in the art based on the teachings herein and information known to the art.

The wall can be a single layer, or can be multiple layers. Materials that should be avoided for manufacture of the wand wall when testing for TCA are: aluminum, anodized aluminum and copper, and non-crystalline plastics such as PVC, polystyrene and polypropylene because these materials absorb or adsorb TCA, or TCA will surface-adhere to these materials, or the plastics out-gas volatiles that corrupt measurements. Materials appropriate to the specific analyte, or analytes, being tested, can be checked for compatibility by one skilled in the art without undue experimentation prior to construction of a wand for specific applications.

The hollow chamber of the wand should be large enough to accommodate a portion or all of the closed container, and still leave a sufficiently large test space to provide enough diffused analyte to be collected by the collection material. In the case of wands for testing single bottles of wine, the test space is generally at least about one cubic centimeter or more. The walls of the wand define the volume of the chamber. The walls can be thicker than required to provide strength and stability, such that all or a portion of the wand can be solid, with only a small chamber hollowed out inside.

The wand comprises a first opening through the wall for receiving all or a portion of the closed container into the chamber of the wand. This opening is sized as required for the specific container desired to be tested, and for best efficiency is as small as possible. The first opening is equipped with a first sealing means operably positioned with respect to the opening to prevent air flow in and out of the chamber through the first opening . . . . In embodiments, the first sealing means comprises a sealing ring that can be fitted within the opening by friction or by structures such as depressions or projections within the first opening. Suitable sealing rings are known to the art, and are made from materials that have suitable properties of strength, flexibility and compressibility, such as Polytetrafluoro-ethylene (PTFE or Teflon), Silicone rubber (VMQ), and Viton® Extreme-ETP (FEPM).

The positioning of the sealing means with respect to the opening may be determined without undue experimentation by one of ordinary skill in the art, and will depend on whether only a portion or the entire closed container is inserted into the chamber, the material of the chamber wall, the material of the container, and other factors known to the art.

The wand also comprises a second opening through the wall for receiving within the test space of the chamber, all or a portion of an analyte-collection material such as a selectively-sorbent fiber. This opening is sized as required for the specific material to be used for collection of the analyte, and should be kept as small as possible. The second opening is equipped with second sealing means operably positioned with respect to the opening to prevent air flow in and out of the chamber through the first opening. In embodiments, the second sealing means comprises an impermeable membrane such as a Polytetrafluoro-ethylene (PTFE or Teflon), Silicone rubber (VMQ), or Viton® Extreme-ETP (FEPM) that may be punctured during the test to insert a selectively-sorbent fiber, and then self-seals around the fiber. In an embodiment, the impermeable membrane is seated on a shelf formed in the concave top of the neck of the wand, which is interiorly threaded, and held in place by tightly screwing a threaded plug down into the threaded neck. Other sealing means and means for positioning these sealing means can be readily determined without undue experimentation by one of ordinary skill in the art, and will depend on the size and shape of the collection material selected for use and the shape of the opening in the wall of the wand, as well as other factors known to the art.

The wand also comprises a third opening through the wall for receiving an air hose or other vacuum conduit for producing a vacuum within the test space of the chamber. This opening is sized as required for the specific size of the wand and suitable conduit to be used for producing the vacuum, and should be kept as small as possible. The third opening is equipped with third sealing means operably positioned with respect to the opening to prevent air flow in and out of the chamber through the third opening (other than air flow through the conduit itself). The third sealing means may be any sealing means known to the art, such as O-rings made of suitable material, including Polytetrafluoro-ethylene (PTFE or Teflon), Silicone rubber (VMQ), and Viton® Extreme-ETP (FEPM). In an embodiment, the wand comprises a vacuum nozzle manufactured integrally to the wand, or welded thereon, and the nozzle is equipped with a gasket to prevent air flow between the outer walls of the vacuum conduit and the inner surface of the nozzle. Other sealing means and means for positioning these sealing means can be readily determined without undue experimentation by one of ordinary skill in the art, and will depend on the size and shape of the vacuum conduit and third opening, the materials they are made of and other factors known to the art.

The vacuum produced inside the test space of the wand chamber should be enough to cause diffusion of a sufficient amount of analyte for the collection material to collect in order to provide an accurate analysis of the presence and amount of analyte in the closed container. A complete vacuum is generally not required. The vacuum can be a vacuum adequate to enhance the rapid sublimation or volatilization of the analyte, but not so large as to cause the seal of the sealed consumables container to break, or the cork to be removed from the bottle in the case of bottles of wine. This is usually a vacuum inside the wand of at about 2 Torr, in the case of TCA, up to a vacuum of about 100 Torr or more for compounds that are more volatile. When a larger container is used, such as the container shown in FIG. 4, the vacuum pressure should be within about these same limits, depending upon the sealing method of the containers being tested and the atmospheric pressure.

The vacuum pump useful as part of the test apparatus described herein can be any vacuum pump known to the art that is capable of producing the required vacuum. The vacuum pump is sealably connected to the third opening in the wand via an airtight conduit. The flow of air through the conduit can be controlled by a valve positioned in operational contact with the conduit, as known to the art for allowing retention and release of vacuum pressure in the chamber of the wand. The vacuum pump is part of a vacuum pump assembly that includes other components such as the conduit, and a valve in operable connection with the conduit. In addition, the vacuum pump assembly can include additional components, such as a trap that allows airflow through and is positioned between the conduit and the vacuum pump. The trap prevents solids and liquids that may have been sucked from the wand and/or container from reaching and interfering with operation of the vacuum pump. The vacuum pump assembly can also include one or more pressure gauges operationally connected thereto for determining whether or not there is vacuum pressure in the system (typically a coarse pressure gauge is used for this purpose), and what vacuum pressure is present in the system (typically a fine pressure gauge is used for this purpose).

The system described herein can also comprise an analyte collection material, which is sized and shaped for insertion into the second opening of said wand. The analyte collection material can be any material that is capable of collecting any expressed, volatile or sublimated chemicals that emerge out of, or off of the sealed container. The analyte collection material is made of or coated with a substance that is selectively-sorptive, or selectively attracts or collects the desired analyte for detection and analysis. Examples of suitable collection materials include polydimethylsilane (PDMS) fibers, and in an embodiment include selectively-sorptive fibers such as solid phase microextraction (SPME) fibers. The analyte collection material can be sized and shaped as required for collecting analyte material in the test space of the chamber of the wand. Especially useful in the wand depicted in the Figures hereof are selectively-sorbent SPME fibers. These are fibers coated with a liquid (polymer), a solid (sorbent) or a combination of both. The fiber coating removes the compounds from the sample by absorption in the case of liquid coatings or adsorption in the case of solid coatings. Selectively-adsorptive and selectively-absorptive fibers are referred to herein as "selectively-sorptive fibers." These fibers are commercially available, packaged in fiber-insertion devices including needles that contain a fiber or at least a portion of a fiber. These assemblies can be purchased from Sigma-Aldrich and include carboxen/polydimethylsiloxane (CAR/PDMS) fibers, polydimethylsiloxane/divinylbenzene (PDMS/DVB) fibers, divinylbenzene/carboxen/polydimethylsiloxane (DVB/CAR/PDMS/fibers, Carbopack-Z fibers, polydimethylsiloxane (PDMS) non-polar fibers, polyacrylate polar (PA) fibers, carbowax-polyethylene glycol (PEG) polar fibers, and carbowax/templated resin (CW/TPR) polar fibers. Each fiber is capable of selectively adsorbing or absorbing specific analytes. For example, polydimethylsilane-coated fibers are useful for adsorbing TCA. For the detection of other chemicals, different selective fibers can be used, e.g., polydimethylsiloxane fibers can be used for the detection of 2,4,6-tribromoanisole, and carboxen fibers mixed with polydimethylsiloxane for the detection of 1-octen-3-one and 1-octen-3-ol. For the detection of other chemicals different selective fibers can be used. Other analyte-collection materials known to the art include cartridge adsorbents and absorbents, also commercially available through Sigma-Aldrich Company. As is known to the art, a wide range of selective sorbents are available that are capable of selectively sorbing desired analytes.

In an embodiment utilizing selectively-sorbent fibers, a fiber-insertion device is used to insert and remove the fiber from the chamber. The fiber-insertion device comprises a needle and plunger in which the needle has a fiber inserted therein. The needle is pushed through the sealing membrane, down into the test space of the wand chamber, and the plunger is used to eject a portion of the fiber into the test space. After allowing the fiber to adsorb or absorb diffused analyte material in the test space, the needle is withdrawn and the fiber is subjected to analysis.

The system described herein can also comprise an analytical instrument capable of identifying the presence and amount of the desired analyte. In some embodiments, a gas chromatography/mass spectrometer (GC/MS) device is used for analysis and identification of substances collected on the analyte collection material. In embodiments, the presence of the analyte is detected; in other embodiments both the presence and amount of the analyte is detected.

Some or all of the above-described system components can be assembled and sold as a unit in the form of a kit comprising a wand and a selective analyte-collection material. A selective analyte-collection material is one that is capable of collecting a desired analyte without collecting other chemicals that would interfere with the analysis of the desired analyte. Desirably, the selective analyte-collection material in the kit is a selectively-sorbent fiber packaged in a fiber-insertion device including a needle and plunger.

Also provided herein is a method for detecting the presence of an analyte in a closed container without opening the container. The method comprises providing a wand as described above, sealably inserting at least a portion of a closed container suspected of containing said analyte into the chamber of said wand through said first opening; sealably inserting a connection to a vacuum pump into the third opening of said wand; operating said vacuum pump to produce sufficient vacuum in said chamber to cause volatilization of an analyzable amount of said analyte into the test space in said chamber; sealably inserting an analyte collection material for said analyte into the second opening of said chamber, whereby said analyte collection material extends into said test space that is under vacuum, allowing sufficient time for an analyzable amount of said analyte to be adsorbed or absorbed onto said analyte-collection material; and removing said analyte-collection material and analyzing it to determine the presence and amount of said analyte.

In embodiments hereof, the analyte-collection material can be inserted into the test space of the wand chamber by hand, for example as described above with respect to the fiber-insertion device, and then removed from the chamber by hand, e.g., by pulling out a needle attached to the fiber in the case of selectively-sorbent fibers. In other embodiments, the placing of the analyte-collection material in the test space of the wand chamber and its removal can be automated using art-known techniques.

The term "sealably inserting" as used herein means that what is inserted is inserted so as not to allow air or gases from inside the wand chamber to escape around the sides of what is inserted. Typically this means that various sealing means as described above are used as part of the system.

The amount of time allowed for selective sorption of the desired analyte within the vacuum produced in the wand chamber is any amount of time that is needed to ensure that an analyzable amount of analyte is collected on the analyte-collection material. An "analyzable amount" may be determined by one of ordinary skill in the art without undue experimentation depending on the analysis device and method used. As discussed above, embodiments of this method are capable of detecting analytes in as low an amount as one part per billion (ppb). In an embodiment hereof involving the collection of TCA from single closed wine bottles, about 15 minutes, plus or minus about 5 minutes is adequate. The testing period can be extended or shortened, depending upon the adsorption rate of the target analyte onto the selective fiber employed, which is generally known from the fiber manufacturer's specifications or can be readily determined by one skilled in the art without undue experimentation.

As discussed above, the container can be a small container capable of fitting entirely within the chamber of the wand, can be a larger container of which only a portion is received within the chamber of the wand, or can be a suction conduit of a large container capable of holding many small containers or items to be tested for the presence of analytes. In an embodiment hereof, the closed container is a corked bottle of wine. The cork may be a natural cork or may be a cork made of synthetic material.

The following embodiments and aspects thereof are described and illustrated in conjunction with systems, tools and methods which are meant to be exemplary and illustrative, not limiting in scope. In various embodiments, one or more of the above-described objectives have been accomplished, while other embodiments are directed to other improvements.

FIG. 1 is a schematic representation of an embodiment of the chemical detection system and process described herein for testing unopened bottles of wine for contamination with 2,4,6-trichloroanisole (TCA). The neck of an unopened bottle of wine 2 is inserted into an insertion opening 31 (seen in FIG. 3) in hollow wand 4. Wand 4 is also equipped with a vacuum opening 18 (seen in FIG. 3) in a vacuum nozzle 20. Vacuum conduit 12 is sealably connected to nozzle 20 and to vacuum pump 6. Conduit 12 is equipped with valve 14 for preventing airflow in and out of wand 4. Vacuum pump 6 is in airflow communication with conduit 12 via trap 16 which prevents liquid and solid contaminants, such as wine that may have accidentally escaped from wine bottle 2, from entering the interior of vacuum pump 6 and interfering with its mechanism. A coarse gauge 10 for determining whether or not the system, including wand 4, is under vacuum pressure, is disposed at the top end of trap 16 between trap 16 and conduit 12. A fine vacuum gauge 8 is also in airflow communication with the system at this point for determining the exact vacuum pressure present in the system, including the vacuum pressure present in wand 4. A fiber-insertion device 36 for inserting a selectively-sorbent fiber 38 (shown in FIG. 3), is inserted through neck 28 of wand 4. Dotted arrow 22 indicates that the selectively-sorbent fiber 38, after exposure to gas present in the hollow chamber 44 (shown in FIG. 3) within wand 4, is then conveyed to gas chromatography mass spectrometer (GC/MS) 50 for analysis of gases sorbed thereon or therein.

Figure 2:
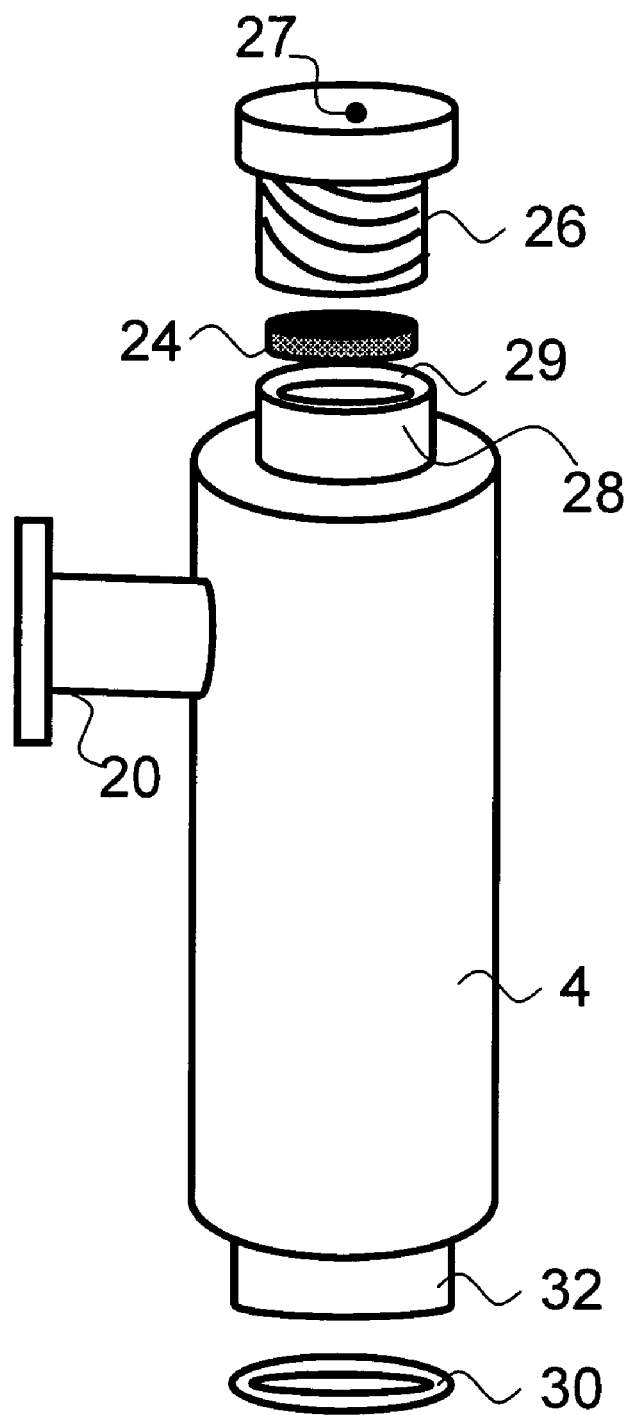
FIG. 2 is an exploded representation of a wand component.

FIG. 2 is an exploded representation of wand component 4, comprising interiorly-threaded neck 28, vacuum nozzle 20, and base 32. A threaded plug 26 is designed to screw into neck 28. Plug 26 is pierced with hole 27 for insertion of the needle component of fiber-insertion device 36. A sealing membrane 24 made of a suitable air-impermeable material such as Teflon or other polymer is designed to be placed on shelf 29 formed by the concave top of neck 28 to make an air-tight seal. A sealing ring 30 is placed within base 32 of wand 4 to allow the neck of a bottle of wine to be inserted into wand 4 in an airtight manner.

Figure 3:
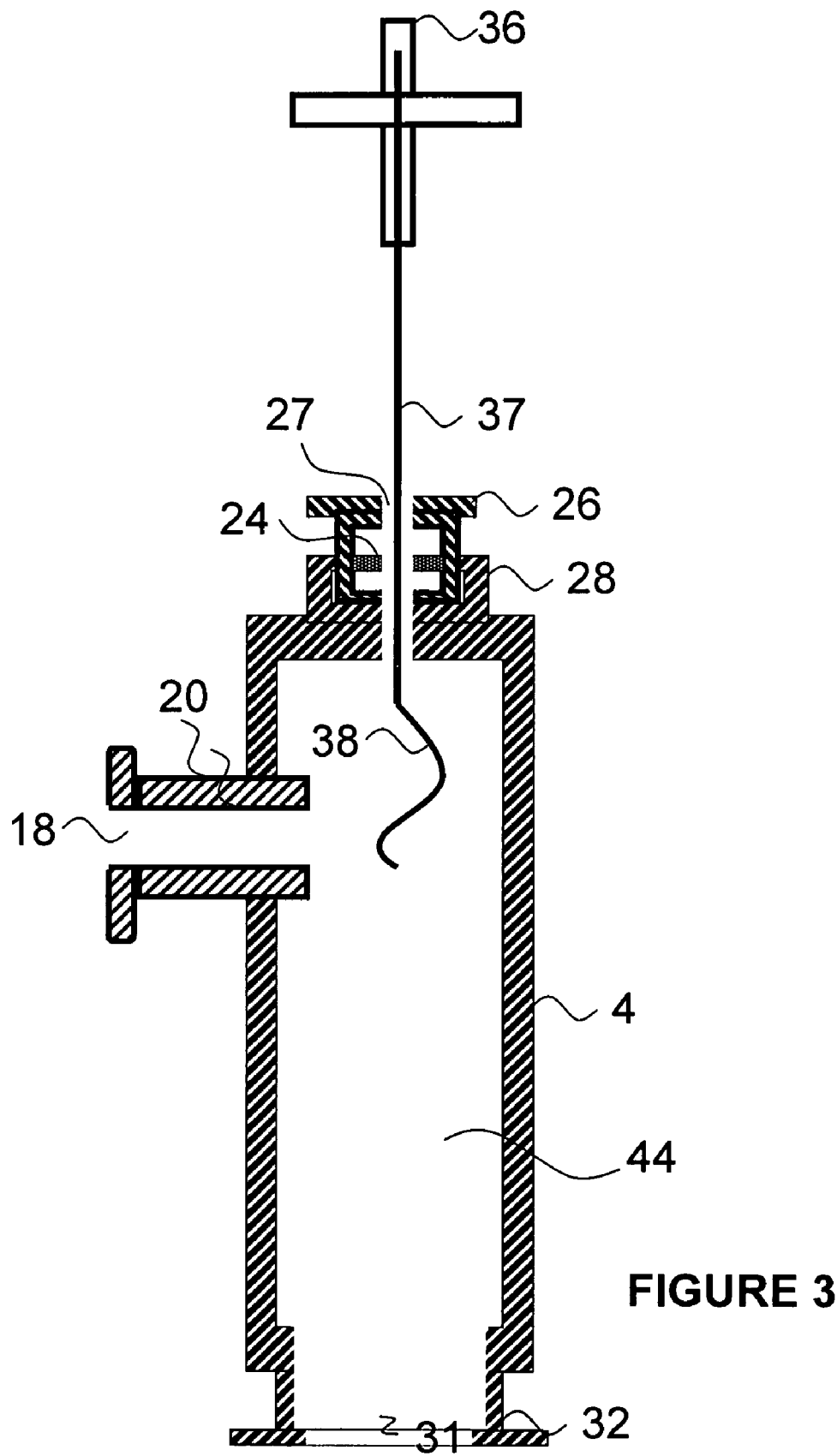
FIG. 3 is a cross-section of a wand component and fiber-insertion device.

FIG. 3 shows a cross-section of wand 4 showing a selectively-sorbent fiber 38 attached to needle 37 of fiber-insertion device 36 comprising selectively-sorbent fiber 38 inserted into chamber 44 of wand 4. Needle 37 extends through hole 27 in plug 26, and through sealing membrane 24 in neck 28. As described above, wand 4 comprises a vacuum opening 18 in nozzle 20, and an insertion opening 31 in base 32.

To assemble the chemical analysis system described herein, sealing membrane 24 is inserted atop shelf 29 formed by the concave top of interiorly-threaded neck 28 of wand 4. Threaded plug 26 is then screwed into neck 28, holding sealing membrane 24 securely in place. The vacuum pump assembly, comprising trap 16, fine pressure gauge 8 and coarse pressure gauge 10, as well as conduit 12 and valve 14, is then placed in air-tight connection with the chamber 44 of wand 4 by inserting conduit 12 into vacuum opening 18 of vacuum nozzle 20 of wand 4. Sealing ring 30 is then inserted into Insertion opening 31 in base 32 of wand 4. Depending on the material used for sealing ring 30 and its size, it may be held in place by friction, or by suitable grooves or projections as known to the art within insertion opening 31. The sealing ring may be made of Polytetrafluoro-ethylene (PTFE or Teflon), Silicone rubber (VMQ), Viton® Extreme-ETP (FEPM), or other materials known to the art.

Figure 4:
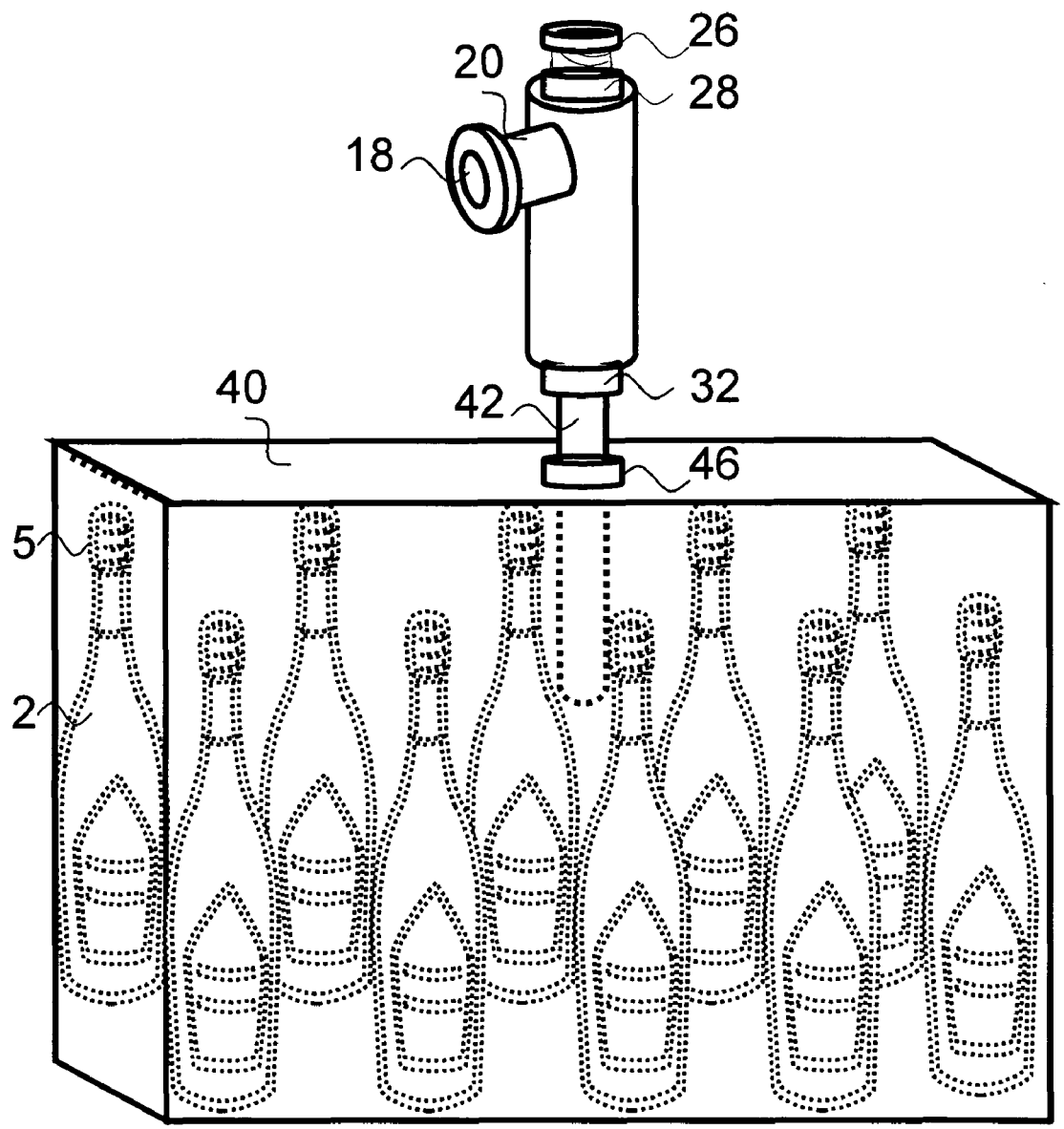
FIG. 4 shows an embodiment of the chemical detection system described herein for testing multiple bottles unopened bottles of wine for TCA contamination.

To operate the chemical analysis system, the neck of an unopened bottle of wine 2, sealed with a cork 5 (as shown in FIG. 4), is inserted through insertion opening 31 in base 32 of wand 4 and through sealing ring 30 into chamber 44 of wand 4 until the neck of the bottle is in snug and air-tight engagement with sealing ring 30, which is in airtight engagement with insertion opening 31, so that no air can flow in or out of the chamber around the neck of wine bottle 2. Vacuum pump 6 is then operated to produce a vacuum in chamber 44 which allows vapors from cork 5 and wine bottle 2 to diffuse into chamber 44. Coarse pressure gauge 10 may first be consulted to determine whether there is a vacuum in conduit 12, i.e., whether valve 14 is open or closed. If valve 14 is closed, it should be opened prior to operating vacuum pump 14. Fine pressure gauge 8 is consulted to determine when the pressure in the chamber has reached the desired level, e.g., between about 2 Torr (for TCA) and about 100 Torr, depending upon the type of container and seal employed thereto, the volatility of the analyte being tested. Pressures different from these may be used for different containers, seals and analytes, and can be readily determined by one skilled in the art in accordance with art-known principles and the teachings herein, noting that maintaining seal integrity under the strain of pressure is important. At that point, valve 14 is closed and vacuum pump 6 is isolated. Needle 37 of fiber-insertion device 36 is then inserted through hole 27 of plug 26 and device 36 is operated to push needle 37 through sealing membrane 24, piercing a hole therethrough. The material of sealing membrane 24 is made of a substance formed in a wafer, such as Teflon (or PTFE) that immediately seals around the outside of the needle to prevent air from entering or escaping through hole 27 of sealing membrane 24. Needle 37 contains a selectively-sorbent fiber 38. The plunger of fiber-insertion device 36 is then operated to eject a portion of fiber 38 into chamber 44.

Fiber 38 is allowed to remain inside chamber 44 for as long as necessary to adsorb TCA that has diffused into chamber 44 from the cork 5 or the wine in wine bottle 2. This period of time can be determined by one of ordinary skill in the art without undue experimentation, and depends on vendor specifications and system parameters such as empirical time-concentration measurements made from intentionally-adulterated corks with known concentrations. In one embodiment, in which the chamber has a size of about 10 cc with the wine bottle neck inserted and the chamber has an air pressure of about 2 Torr, fiber 38 remains in chamber 44 for about 10 to 15 minutes. The fiber-insertion device 36 is then used to pull the attached selectively-sorbent fiber 38 out of the chamber 44. The fiber is removed by hand and transported to the GC/MS for analysis to determine whether a contaminating level, i.e., between about $10^{-9}$ g/L and about $10^{-6}$ g/L of TCA is present in the container. It has been found that generally when any one bottle of wine is contaminated with TCA, many of the bottles that were produced by the same winery at the same time will be found to also be contaminated.

FIG. 4 shows an embodiment of the chemical detection system described herein for testing multiple unopened bottles of wine for TCA contamination. Multiple bottles of wine 2, each sealed with a cork 5, are placed in a container 40. Container 40 comprises as an integral part thereof, or is sealably connected by means of gasket fitting 46 to a suction conduit 42 that sealably fits into base 32 (equipped with sealing ring 30 shown in FIG. 2) of wand 4. Wand 4 is connected to the vacuum pump assembly as described above and vacuum pump 6 (shown in FIG. 1) is operated until the desired vacuum is produced in container 40 so that a detectable level of TCA, if present, will diffuse into the space inside container 40. The fiber-insertion device 36 is then operated to insert a selectively-sorbent fiber 38 into the interior of container 40, and fiber 38 is allowed to remain there for an appropriate period, e.g., between about 10 to 15 minutes to allow it to adsorb detectable levels of TCA. The fiber 38 is then removed as described above and subjected to GC/MS analysis to determine whether or not a contaminating level, i.e., between about $10^{-9}$ g/L and $10^{-6}$ g/L of TCA is present in the container.

Example

Wine bottles were tested for TCA contamination using the system described above. A calibration experiment comparing TCA contaminated corks not inserted into wine bottles ("Free Corks") and corks inserted into wine bottles ("Bottled Corks") was conducted as follows: TCA-tainted corks for testing were prepared by exposure to TCA and ethyl alcohol. The tainted corks were each tested separately using the system described above, sealing the insertion opening of the wand with a stainless steel plug, and placing each cork in the chamber of the wand. Then the tainted corks were pounded tightly into bottles of wine, the necks of the wine bottles were inserted into the insertion opening of the wand, and the test was run again. TCA collection on the fiber was allowed for a period of about 15 minutes at a reduced pressure of about 2 Torr. Following each method of exposure, a fresh fiber was retracted into the needle and withdrawn, removed from the wand, and placed into the injection port of a Varian Model 2100T GC/MS equipped with a column capable of separating TCA from other compounds on the basis of retention time at elevated temperature. Combining this separation with the MS capability of the GC/MS leads to an extremely sensitive, background-free TCA-selective measurement as shown in Table 1 for TCA-adulterated corks both in and out of a wine bottle. "Free Corks" as referred to in Table 1 are the tainted corks by themselves, placed in the sealed chamber of the wand. "Bottled Corks" are the same tainted corks pounded tightly into the necks of bottles of wine. The presence of a foil wrapper did not alter these results when the experiment was repeated with a foil cap.

TABLE 1

Summary of Free Cork and Bottled Cork TCA Measurements

| TCA in Cork | TCA Signal (counts) | |
| --- | --- | --- |
| (ng) | Free Cork | Bottled Cork |
| 8 | 543 | 564 |
| 28 | 2959 | 2419 |
| 95 | 6215 | 3466 |
| 155 | 8274 | 8083 |

This test shows that the apparatus and method described herein is capable of easily detecting down to 8 ng of TCA in corks, nearly an order of magnitude lower than the mass of TCA expected to be in corks that lead to tainted wine. The data shows that about the same amount of TCA can be detected whether or not the tainted cork has been removed from the bottle. It has also been determined that foil-wrapped corks can also be effectively tested using the system and method described herein. The presence of a foil cap does not significantly prevent diffusion of TCA into the chamber of the wand.

Similar tables to Table 1 are developed for other chemicals targeted for detection, and the number of counts (signal) as a function of exposure time of the collector to the sample is determined on the basis of physical data and experimental trials by one skilled in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

REFERENCES

1. A. Martinez-Urunuela, J. M. Gonzalez-Saiz, and C. Pizarro, "Multiple solid-phase microextraction in a non-equilibrium situation: Application in quantitative analysis of chlorophenols and chloroanisoles related to cork taint in wine", Journal of Chromatography A, 1089, 2005, 31-38.
2. J. L. Gomez-Ariza, T. Garcia-Barrera, and F. Lorenzo, "Optimization of a two-dimensional on-line coupling for the determination of anisoles in wine using ECD and ICP-MS after SPME-GC separation", Journal of Analytical Atomic Spectrometry, 20, 2005, 883-888.
3. P. R. Howland, A. P. Pollnitz, D. Liacopoulos, H. J. McLean, and M. A. Sefton, "The location of 2,4,6-trichloroanisole in a batch of contaminated wine corks", Australian Journal of Grape and Wine Research, 3, 1997, 141-145.

The invention claimed is:

1. A wand in combination with a closed container, said wand adapted to detect the presence of an analyte from within said closed container without opening said container, said wand comprising:
    a wall defining a hollow chamber within said wand, wherein said chamber is sized to accommodate at least a portion of said closed container, leaving a test space within said chamber;
    a first opening in said wall sized and shaped for receiving at least a portion of said closed container within said chamber during testing for an analyte present in said closed container without opening said container;
    first sealing means operably positioned with respect to said first opening for sealing said first opening so as to prevent air flow in and out of said chamber through said first opening;
    a second opening in said wall for receiving within said test space at least a portion of an analyte collection material capable of adsorbing or absorbing said analyte within said test space;
    second sealing means operably positioned with respect to said second opening for sealing said second opening so as to prevent air flow in and out of said chamber through said second opening;
    a third opening in said wall for receiving a conduit for creating at least a partial vacuum in said test space; and
    third sealing means operably positioned with respect to said third opening for sealing said third opening so as to prevent air flow other than through said conduit in and out of said third opening; and
    wherein both said closed container and said wand lack a valve or flow control connector for opening and closing flow between said closed container and said chamber.

2. The combination of claim 1 wherein said first sealing means is capable of sealing said first opening in contact with a portion of said closed container.

3. The combination of claim 1 wherein said first opening and first sealing means are sized and shaped to receive the neck of an unopened, corked bottle of wine.

4. A system for detecting the presence of an analyte in a closed container without opening the container, comprising:
    the combination of claim 1; and
    a vacuum pump sealably connected to said third opening of said wand via an airtight conduit.

5. The system of claim 4 also comprising a valve in operable connection with said airtight conduit for allowing retention and release of vacuum pressure in said chamber.

6. The system of claim 4 also comprising an analytical instrument capable of identifying the presence and amount of said analyte.

7. The system of claim 6 wherein said analytical instrument is a gas chromatography/mass spectrometer for analyzing a chemical adsorbed or absorbed on or in said selectively sorbent fiber.

8. The system of claim 4 also comprising said analyte collection material, which is sized and shaped for insertion into said second opening of said wand.

9. The system of claim 8 wherein said analyte collection material is selected from the group consisting of solid-phase microextraction (SPME) fibers, carboxen/polydimethylsiloxane (CAR/PDMS) fibers, polydimethylsiloxane/divinylbenzene (PDMS/DVB) fibers, divinylbenzene/carboxen/polydimethylsiloxane (DVB/CAR/PDMS/fibers, Carbopack-Z fibers, polydimethylsiloxane (PDMS) non-polar fibers, polyacrylate polar (PA) fibers, carbowax-polyethylene glycol (PEG) polar fibers, and carbowax/template resin (CW/TPR) polar fibers.

10. The system of claim 8 wherein said analyte collection material is a selectively-sorbent fiber.

11. The system of claim 10 wherein said selectively-sorbent fiber is packaged in an insertion needle.

12. A kit comprising:
    the combination of claim 1; and
    a selectively-sorbent fiber packaged in an insertion needle for inserting said fiber into the second opening of said wand.

13. A method for detecting the presence of an analyte in a closed container without opening the container, said method comprising:

(a) providing a wand for detecting the presence of an analyte in a closed container without opening the container, said wand comprising:
  a wall defining a hollow chamber within said wand, wherein said chamber is large enough to accommodate at least a portion of said closed container, leaving a test space within said chamber;
  a first opening in said wall for receiving at least a portion of said closed container within said chamber;
  first sealing means operably positioned with respect to said first opening for sealing said first opening so as to prevent air flow in and out of said chamber through said first opening;
  a second opening in said wall for receiving within said test space at least a portion of an analyte collection material capable of adsorbing or absorbing said analyte within said test space;
  second sealing means operably positioned with respect to said second opening for sealing said second opening so as to prevent air flow in and out of said chamber through said second opening;
  a third opening in said wall for receiving a conduit for creating at least a partial vacuum in said test space; and
  third sealing means operably positioned with respect to said third opening for sealing said third opening so as to prevent air flow other than through said conduit in and out of said third opening;
(b) sealably inserting at least a portion of a closed container suspected of containing said analyte into the chamber of said wand through said first opening;
(c) sealably inserting a connection to a vacuum pump into the third opening of said wand;
(d) operating said vacuum pump to produce sufficient vacuum in said chamber to cause volatilization of an analyzable amount of said analyte into the test space in said chamber;
(e) sealably inserting an analyte collection material for said analyte into the second opening of said chamber, whereby said analyte collection material extends into said test space;
(f) allowing sufficient time for an analyzable amount of said analyte to be sorbed by said analyte collection material; and
(g) removing said analyte collection material and analyzing it to determine the presence and amount of said analyte.

14. The method of claim 13 wherein said analyte collection material is a selectively-sorbent fiber.

15. The method of claim 13 wherein analyzing of said analyte collection material is done via GC/MS.

16. The method of claim 13 wherein said analyte is 2,4,6-trichloroanisole (TCA).

17. The method of claim 13 wherein said closed container is a "stream-of-commerce" container.

18. The method of claim 17 wherein said closed container is capable of holding multiple "stream of commerce" containers.

19. The method of claim 17 wherein said closed container is a corked bottle of wine.

* * * * *